United States Patent [19]

Nakada et al.

[11] Patent Number: 4,558,706
[45] Date of Patent: Dec. 17, 1985

[54] DEVICE FOR DIAGNOSING BODY CAVITY INTERIORS WITH ULTRASONIC WAVES

[75] Inventors: Akio Nakada, Hachioji; Kazumasa Matsuo, Tama, both of Japan

[73] Assignee: Olympus Optical Co., Ltd., Tokyo, Japan

[21] Appl. No.: 472,496

[22] Filed: Mar. 7, 1983

[30] Foreign Application Priority Data

Mar. 5, 1982 [JP] Japan .................................. 57-34773

[51] Int. Cl.⁴ ............................................. A61B 10/00
[52] U.S. Cl. ........................................ 128/660; 128/4
[58] Field of Search .................. 128/660, 4, 638, 6; 73/633, 634; 277/72 FM, 205; 308/187

[56] References Cited

U.S. PATENT DOCUMENTS

| | | | |
|---|---|---|---|
| 3,012,829 | 12/1961 | Marshall | 277/205 |
| 3,155,091 | 11/1964 | Nissenbaum et al. | 128/638 |
| 3,199,876 | 8/1965 | Magos et al. | 277/72 FM |
| 4,177,998 | 12/1979 | Laitkep et al. | 277/72 FM |
| 4,316,271 | 2/1982 | Evert | 128/660 |
| 4,374,525 | 2/1983 | Baba | 128/660 |
| 4,391,282 | 7/1983 | Ando et al. | 128/660 |

FOREIGN PATENT DOCUMENTS 766516  1/1957  United Kingdom .......... 277/72 FM

Primary Examiner—William E. Kamm
Assistant Examiner—Ruth S. Smith
Attorney, Agent, or Firm—Armstrong, Nikaido, Marmelstein & Kubovcik

[57] ABSTRACT

A device for diagnosing body cavity interiors with ultrasonic waves consisting of an ultrasonic wave transmitter and receiver in a housing chamber filled with a wave transmitting fluid and coated with a jacket cover and connected to the end of a flexible tube for insertion into a body cavity, the flexible tube having a light source for illuminating a portion of a body cavity, a light guide for viewing the illuminated cavity portion and a cable for transmitting energy to and receiving readings from the wave transmitter and receiver, the wave transmitter and receiver including an ultrasonic wave mirror having a reflection surface for transmitting and receiving ultrasonic waves and a recess in a surface of the mirror at the rear of the reflection surface for collecting gas bubbles generated in the transmitting fluid, a conduit from the housing chamber to the outside of the chamber for filling the chamber with fluid, a removable closure for the conduit, the conduit and closure being within the jacket cover and not extending therebeyond and seals at the end of the flexible tube between the tube end and the housing chamber for sealing the tube end and the chamber.

5 Claims, 9 Drawing Figures

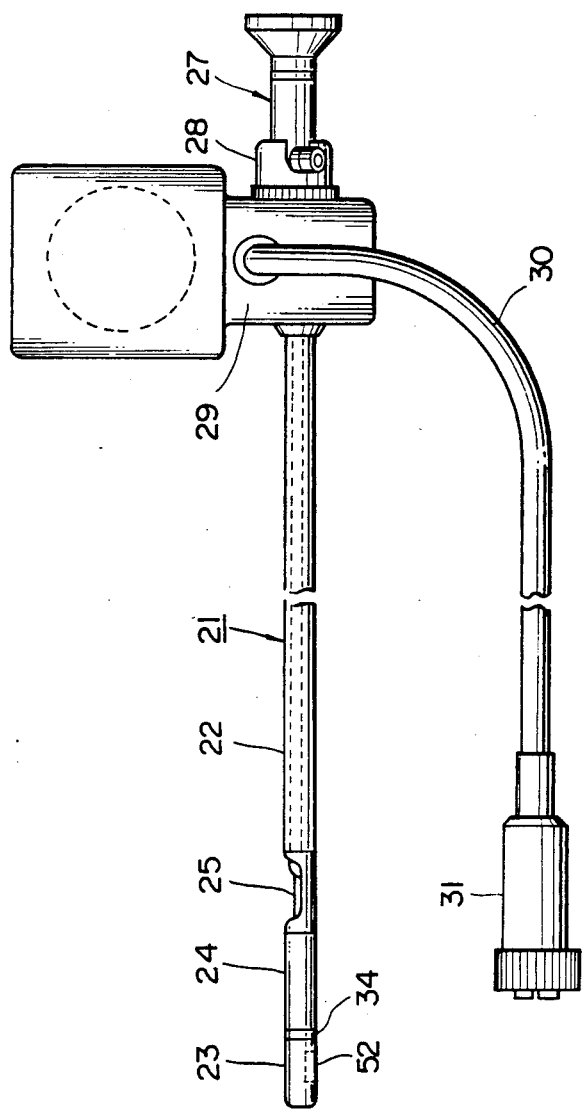

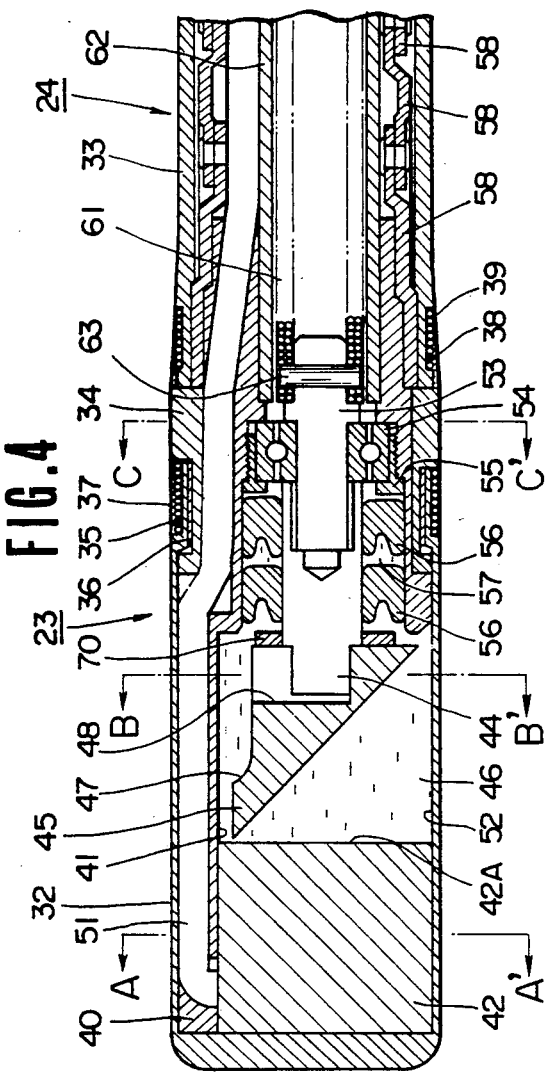

DEVICE FOR DIAGNOSING BODY CAVITY INTERIORS WITH ULTRASONIC WAVES

BACKGROUND OF THE INVENTION

This invention relates to a device for diagnosing body cavity interiors with ultrasonic waves wherein an ultrasonic wave transmitting medium can be put in and out and an opening end facing the outside is sealed with a closing member which can be opened and closed.

An ultrasonic wave diagnosing device wherein ultrasonic waves are transmitted and received to diagnose acoustic information within a body cavity has recently come to be used together with an endoscope wherein the inserted part is inserted into the body cavity so as to be able to optically observe the body cavity interior or to cure it by using a forceps.

In this ultrasonic wave diagnosing device, when ultrasonic wave pulses are projected into a body, for example, form the body surface and the projected ultrasonic waves propagate, they will be reflected by a discontinuous boundary surface of an acoustic impedance represented by the product of the density of the medium and the sound velocity. Therefore, the above mentioned reflected ultrasonic wave pulse waves can be received and such acoustic information as the reflection intensity can be utilized for a diagnosis.

As compared with an X-ray device, such an ultrasonic wave diagnosingdevice has many advantages in that information on a living body soft structure can be easily obtained without using a forming agent, that the living body structure will not be destroyed by radioactive, and that the device is easier to handle and is less dangerous. Further, with the recent improvements of the quality and quantity of the information generated by the progress of the technique on ultrasonic waves, this device is becoming popular as a clinical diagnosing device in the medical field.

In comparison diagnosis wherein ultrasonic wave pulses are transmitted and received on the above mentioned body surface, a method of diagnosing body cavity interiors with ultrasonic waves has been developed wherein ultrasonic wave pulses are transmitted and received in a position near a living body organ within the body cavity. In such a method, high frequency ultrasonic waves which are (comparatively) large in attenuation with propagation can be transmitted and received. Many advantages result such as information of a disintegratability and high precision can be obtained and that the method will not be influenced by a hypodermic fat layer or the like interposed between objects and therefore this method will be used more and more in the future. It is general that this body cavity interior ultrasonic wave diagnosing device to be used as introduced into a body cavity is used integrally with an endoscope as an optically observing means or as fitted with a removable endoscope (optical sighting tube).

In the above mentioned body cavity interior ultrasonic wave diagnosing device, an ultrasonic wave oscillator or the like transmitting and receiving ultrasonic waves is contained within a probe head coated with a jacket cover on the tip side of an ultrasonic probe to be introduced into a body cavity and a transmitting medium transmitting ultrasonic waves is put in to fill the space around the ultrasonic wave oscillator or the like and, when bubbles are mixed into the transmitting medium or the characteristics of the transmitting medium deteriorate, the image quality of the obtained ultrasonic wave fault image will reduce and therefore the operations of removing the bubbles and putting in and out the transmitting medium will be required. However, in a conventional body cavity interior ultrasonic wave diagnosing device, the above mentioned operations have been difficult.

BRIEF SUMMARY OF THE INVENTION

An object of the present invention is to provide a device for diagnosing body cavity interiors with ultrasonic waves wherein an ultrasonic wave transmitting medium can be easily replaced.

Another object of the present invention is to provide a device for diagnosing body cavity interiors with ultrasonic waves wherein bubbles mixed in an ultrasonic wave transmitting medium can be easily removed.

Further, another object of the present invention is to provide a device for diagnosing body cavity interiors with ultrasonic waves wherein an ultrasonic wave transmitting medium can be well sealed in the device.

Further objects and features of the present invention will become apparent enough from the following description.

BRIEF DESCRIPTION OF THE DRAWINGS

FIG. 1 is a sectioned view showing the tip portion of an inserted portion of the prior art example.

FIG. 2 is a perspective view showing the tip portion of the inserted portion with a jacket cover removed.

FIGS. 3 to 9 relate to an embodiment of the present invention.

FIG. 3 is a schematic perspective view of the embodiment in which an ultrasonic wave probe body is fitted with an optical sighting tube.

FIG. 4 is a longitudinally sectioned view showing the structure of an ultrasonic wave probe head in the embodiment.

FIG. 5 is a cross-sectioned view on line A—A' in FIG. 4.

FIG. 6 is a cross-sectioned view on line B—B' in FIG. 4.

FIG. 7 is a cross-sectioned view on line C—C' in FIG. 4.

FIG. 8 is a longitudinally sectioned view on line O-D in FIG. 7 showing the periphery of a communicating hole portion for replacement of a transmitting medium.

FIG. 9 is a longitudinally sectioned view on line O-E in FIG. 7 showing the periphery of the communicating hole portion for replacement of the grease.

DESCRIPTION OF THE PREFERRED EMBODIMENT

Figure 1:
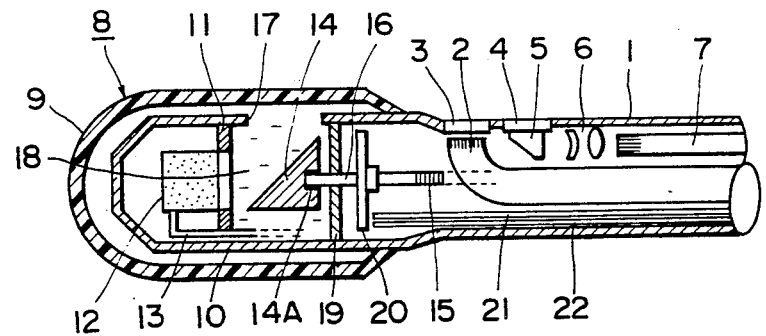
FIGS. 1 and 2 relate to a prior art example.

Prior to explaining the embodiment of the present invention, a conventional example of a device for diagnosing body cavity interiors with ultrasonic waves shall be explained with reference to FIGS. 1 and 2.

In these drawings, a tubular inserted portion 1 forming an ultrasonic wave probe contains an observing optical system, an illuminating optical system, an ultrasonic wave mirror rotating shaft an electric transmitting signal cable and optical fibers connected to an ultrasonic wave oscillator.

A flexible light guide 2 formed of a glass fiber bundle or the like transmitting an illuminating light from an external light source (not illustrated) is inserted through the above mentioned inserted part 1 and is curved at the tip. A glass window 3 is made through the inserted portion in front of the end surface of the light guide 2 so that the illuminating light may be projected into a body cavity through this glass window 3.

On the other hand, as an optical system for observing internal organs illuminated by the illuminating light, the inserted portion 1 is provided with a second glass window 4 which is substantially adjacent to the above mentioned glass window 3, a right angle prism 5 in contact with the inside surface of the second glass window 4, an image forming lens system 6 for forming an image of the incident light reflected at right angles through the prism 5 and an image guide 7 formed of a bundle of very fine glass fibers transmitting the optical image formed by the lens system 6 so that the interior of the cavity can be observed from outside through this image guide 7.

A means for transmitting and receiving ultrasonic waves while rotating is contained in an ultrasonic wave probe head 8 at the tip of the inserted portion 1.

The wave probe head 8 is covered with a soft jacket cover 9 formed of a material such as a rubber or organic resin which can be in close contact directly with living tissue such as a stomach wall to effectively transmit and receive ultrasonic wave beams. A casing tube 10 formed of a metal or the like is contained with the jacket cover 9.

The casing tube 10 contains an ultrasonic wave oscillator 12 supported by a supporting member 11 fixed at its periphery with the tube 10 so as to generate and receive ultrasonic waves and convert them to electric signals, a signal cable 13 connected to the ultrasonic wave oscillator 12 so as to transmit electric signals, an ultrasonic wave mirror 14 reflecting ultrasonic wave beams and transmitting them in the direction at right angles and a shaft 16 rotating the above mentioned ultrasonic wave mirror 14 through a flexible coil wire 15 transmitting the rotation by a motor provided outside of the head. In the above mentioned ultrasonic wave mirror 14, a screw hole 14A is formed so as to be screwed with a screw portion formed at the tip of the shaft 16 so that the ultrasonic wave mirror 14 can be engaged and disengaged with the shaft 16 by being rotated.

The above mentioned ultrasonic wave oscillator is formed of a piezoelectric material such as quartz or PZT (a solid solution of lead zirnonate $PbZrO_3$ and lead titanate $PbTiO_3$) so as to generate ultrasonic waves when impressed with electric signals or generate electric signals when excited by ultrasonic waves. The ultrasonic wave mirror 14 having a reflecting surface inclined at an angle of 45 degrees for reflecting the ultrasonic wave beam substantially at right angles is arranged opposed to the transmitting and receiving surface of this ultrasonic wave oscillator 12.

Figure 2:
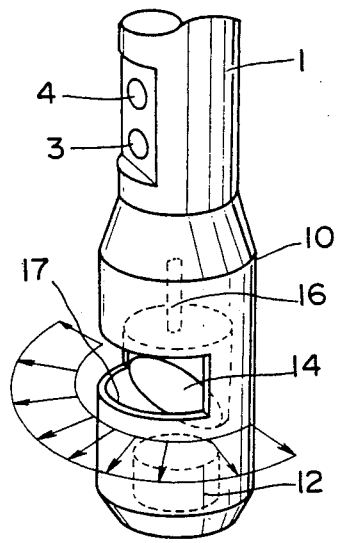

An opening window 17 is made in the tube 10 along the rotary transmitting and receiving surface of the ultrasonic wave mirror 14 so that the ultrasonic wave beam generated by the ultrasonic wave oscillator 12 may be projected (transmitted) in a wide range (for example, about 180 degrees) of directions (as indicated by the arrows in FIG. 2). An ultrasonicwave transmitting medium 18 such as saline water or olive oil having substantially the same value as of the acoustic impedance as an organ within a living body is put in to fill the space around the transmitting and receiving surface of the ultrasonic wave oscillator 12 and the ultrasonic wave mirror 14 so that ultrasonic waves may be effectively transmitted. This transmitting medium 18 fills the interior of a balloon-like jacket cover 9 through the above mentioned opening window 17 and is sealed and intercepted by a sealing member 19 so that the transmitting medium around the ultrasonic wave mirror 14 may not leak to the observing optical system side. A disk indicated by the reference numeral 20 is fixed to the shaft 16 so as to rotate integrally with the ultrasonic wave mirror 14 and is provided on one surface with a reflecting portion having fine streaks. Two optical fibers 21 and 22 are arranged as opposed to this reflecting portion. One optical fiber 21 leads a light from an external light source to illuminate the surface provided with the above mentioned reflecting surface of the disk 20. On the other hand, the other optical fiber 22 feeds the light reflected by the reflecting portion to an external controlling device (not illustrated) so as to sign the beginning of the sector scanning of ultrasonic waves with the signal of the reflected light.

In the conventional body cavity interior ultrasonic wave diagnosing device formed as in the above, there have been problems that the shapes of the ultrasonic wave oscillator 12 and ultrasonic wave mirror 14 contained in the ultrasonic wave probe head 8 are so small that the intensity of the transmitted and received ultrasonic waves will weaken and the signal/noise ratio of the indicated ultrasonic wave fault image will reduce.

Therefore, the above mentioned ultrasonic wave oscillator 12 and ultrasonic wave mirror 14 are made to be of sizes approaching the inner peripheral surface of the tube 10 so that the intensity of the ultrasonic waves may not reduce in the use.

When such conventional ultrasonic wave probe is used over a long period, image quality is reduced by problems such as gases dissolved in the transmitting medium 18 within the jacket cover 9, bubbles mixing in when the degree of sealing is not sufficient, bubbles mixing in during repair and maintenance and deposited on the inner peripheral surface of the jacket cover 9 and the inner and peripheral surfaces of the outer tube 10, bubbles adsorbed on the tube 10 or the like when gases are not vented well, bubbles mixing in the transmitting medium 18 in the advancing course of the ultrasonic waves as the transmitting medium 18 is agitated when the ultrasonic waves are transmitted and received by rotating the ultrasonic wave mirror 14 or bubbles deposited on the ultrasonic wave mirror 14. Such problems may result in a misdiagnosis.

Also, if the transmitting medium 18 leaks to the observing optical system side, the observed image will become unclear and the transmitting medium will have to be supplemented. Further, in case the characteristics of the transmitting medium 18 deteriorate, the transmitting medium 18 will have to be replaced.

In the conventional ultrasonic wave probe, the above mentioned transmitting medium 18 can not be simply replaced and the bubbles are difficult to remove.

The present invention is made to solve the problems of the above mentioned conventional example.

The device for diagnosing body cavity interiors with ultrasonic waves of the embodiment of the present invention shall be described in the following with reference to FIGS. 3 to 9.

In these drawings, an ultrasonic wave probe (body) 21 as shown in FIG. 3, comprises an elongate inserted portion 22 to be inserted (introduced) into a body cavity, a tubular ultrasonic wave probe head 23 having the function of transmitting and receiving ultrasonic waves and a bendable portion 24 are connected with each other. An incised window 25 is made on the outer periphery of the inserted portion 22 in the rear of this bendable portion 24. A guide tube (for an optical sighting tube) is fitted and inserted from the rear end of the inserted portion 22 to the incised window 25 so that an optical sighting tube (scope) 27 may be removably fitted in the guide tube.

An operating portion 28 for inserting and removing the optical sighting tube 27 is provided at the rear end of the probe body 21. A holding grip 29 is provided oriented upward vertically to the axial direction of the inserted portion and contains a rotating driving motor, a head amplifier for amplifying at low noise the signal received as separated from the motor and a rotation detector detecting the rotating position of a shaft rotated by the motor. An angle knob for curving the above mentioned bendable portion 24 is fitted to the side part (the back surface side in FIG. 3) of the holding grip 29. A cable 30 for transmitting electric power for the rotating driving motor and for transmitting the signal transmitting and receiving ultrasonic waves extends out of the side part opposite the side to which the angle knob is fitted and is fitted at its tip with a liquid-tight connector 31 so as to be able to be washed or disinfected.

The structure of the ultrasonic wave probe head 23 is as shown in FIG. 4.

The ultrasonic wave probe head 23 is covered on the tip side with a soft tubular jacket cover 32 closed on the tip side, open on the rear end side and made of a polyethylene or the like. This jacket cover 32 is kept liquid-tight in the rear end portion by a thread-like member 35 wound in a recessed step of a ring-shaped connecting fixing member 34 interposed on the outer pheriphery of a tip block 40 near the boundary with a coating tube 33 on the outer periphery of the bendable part 24 and can be fixed so strongly as not to come out of the step.

That is to say, the above mentioned jacket cover 32 is made smaller in diameter in the form of a step on the periphery of the rear end part, and this smaller diameter step is fitted to the recessed step of the connecting fixing member 34 hearing a soft tube 36 high in the elasticity fitted therearound. The cover 32 is strongly fixed in the end part by the above mentioned thread-like member 35 wound on the recessed step so as to improve the liquid-tightness. The outer peripheral recess of this wound thread-like member 35 is painted on the outer peripheral recess with a bonding agent. A recessed step is formed also near the end of the soft coating tube 33 adjacent to the above mentioned connecting fixing member 34. A thread-like member 38 is wound on this step and is painted with a bonding agent 39 in the outer peripheral recess. Thus, the soft jacket cover 32 on the tip side and the soft coating tube part 24 are not connected directly with each other but have a ring-shaped connecting fixing member 34 having a sufficient strength interposed between them so that the jacket cover 32 and coating tube 33 may be strongly held further, when they are repeatedly inserted and removed or when the jacket cover 32 on the tip side or the coating tube 33 on the outer pheriphery of the bendable part 24 is worn or broken, only the part may be replaced by unwinding the above mentioned wound thread-like members 35 and 38.

A housing chamber 41 is formed in a hollow tip block (member) 40 covered with the cover 32 forming the above mentioned outer pheriphery. Within this housing chamber 41, an ultrasonic wave oscillator 42 transmitting and receiving ultrasonic waves is fixed to the above mentioned tip block 40 with a screw 43 or the like (FIG. 5). A rotatable and removable (ultrasonic wave) mirror 45 is fitted to the tip part of a first shaft 44 rotated and driven to scan ultrasonic waves. The mirror 45 can be inclined, for example, at 45 degrees with the ultrasonic wave transmitting and receiving surface 42A of this ultrasonic wave oscillator 42.

The above mentioned mirror 45 has as an ultrasonic wave reflecting surface made by diagonally cutting a columnar member and has an incised recess 47 as shown in FIGS. 4 and 6 formed in a part on the back surface side of this reflecting surface so as to be easy to collect and remove bubbles produced within the (ultrasonic wave) transmitting medium 46 such as an aqueous solution of sucrose put in to fill the housing chamber 41 around the mirror 45. If an aqueous solution of sucrose of a concentration of about 5 to 15% is used for the transmitting medium, the respective members will be better protected from rusting than with saline water or the like, the acoustic impedance will be able to be made substantially equal to that of a living body, enabling ultrasonic waves to be efficiently transmitted, and the aqueous solution will have less loss components to the propagation of ultrasonic waves than oil or the like thereby presenting the reduction of the intensity of ultrasonic wave beams during propagation.

A guide groove 48 is formed on the base side of the mirror 45 so that the mirror can be fitted to and removed from the rotating shaft 44 by being inserted and removed in the direction at right angles with the shaft 44 and can be removably fixed to the shaft 44 with screws 50 screwed into screw threaded holes 49 (FIG. 6).

A cable 51 for transmitting signals for transmitting and receiving ultrasonic waves is connected to the above mentioned ultrasonic wave oscillator 42, is inserted through the inserted portion 22 to the holding grip 29 and is finally connected with an external indicating device through a cable (external) 30 from the holding grip 29 side.

A window 52 for transmitting and receiving ultrasonic waves is formed by making an opening in a part of the side wall of the housing chamber 41 formed of the tip block 40 around the above mentioned mirror 45 so that the ultrasonic wave beam sent out of the transmitting and receiving surface 42A of the ultrasonic wave oscillator 42 will be reflected by the mirror 45 and will be emitted out of the opening, that is, the transmitting and receiving window 52 in the tip block 40 through the jacket cover 32. On the other hand, a part of the ultrasonic waves reflected by the discontinuous boundary surface of the external acoustic impedance will be reflected by the mirror 45 and will be incident upon the ultrasonic wave oscillator 42.

The above mentioned mirror 45 can be pulled off along the guide groove 48 and can be taken out of the above mentioned transmitting and receiving window 52 for easy maintenance and repair.

The above mentioned mirror 45 is fitted to the tip of the first shaft 44 screwed onto a second shaft 53 rotatably borne by a bearing 54. This bearing 54 contacts on the rear end side with a locking part projected inside the tip block 40 and a projection formed on the second shaft 63 and is supported at the other end with a ring-shaped lock screw 55 so as not to move forward and rearward.

Sealing members 56 substantially U-shaped in cross-section are annularly fitted in an annular air gap part between the outer peripheral surface of the above mentioned first shaft 44 and the inner wall surface of the tip block 40. These respective sealing members 56 are elastic members so as to be biased inward and outward in the radial direction in both end parts of the U-shape and to contact in both end parts of the U-shape with the inner and outer peripheral surfaces. On the other hand, a grease charged chamber 57 formed between one U-shaped recess 56 and the other sealing member 56 is charged with such grease as Moricoat Grease to prevent the transmitting medium 46 from leaking to the bearing 54 side and to extremely control the friction resistance in case the shaft 44 in contact with the sealing members 56 rotates so that the shaft 44 may smoothly rotate.

Many articulated frames 58 rotatably connected in the pivoted parts on both sides (above and below in FIG. 4) adjacent to each other are contained within the bendable portion 24 coated with the above mentioned coating tube 33 so that the bendable portion 24 can be bent in the direction vertical to the paper surface in FIG. 4 (rightward and leftward) by drawing and relaxing an operating wire (not illustrated).

On the other hand, the articulated frame 58 at the tip in the above mentioned bendable portion 24 is fixed on the outer peripheral surface at the rear end of the tip block 40. A soft shaft 61 connected at the front end with the above mentioned second shaft 53 and at the other end with a hard shaft (not illustrated) is inserted through a soft tube 62 in the inside hollow part in which the articulated frames 58 from the fixed part to the incised window 25 shown in FIG. 3 are connected.

The above mentioned soft shaft 61 is formed of two inside and outside wound layer coils. These inside and outside coils are wound reversely to each other so that the outside diameter will not vary with the rotating direction and the rotation will be able to be effectively transmitted even when curved. This soft shaft 61 is fixed at the end by soldering or silver brazing so as to be easy to be drilled, is then holed at the end with a drill or the like in the direction at right angles with the axial direction, is externally fitted to the second shaft 53 from the rear end side until it contacts the projection, and is connected with the second shaft through a pin 63 passed and fixed through the above mentioned holes and a hole made in the second shaft 53 so that the rotation of the soft shaft 61 may be transmitted to the second shaft 53 side. This soft shaft 61 is covered on the outer pheriphery with a soft tube 62 molded of Teflon or the like low in the friction even in contact on the inner peripheral surface with the rotating soft shaft 61 and endurable to curving or the like.

Figure 8:
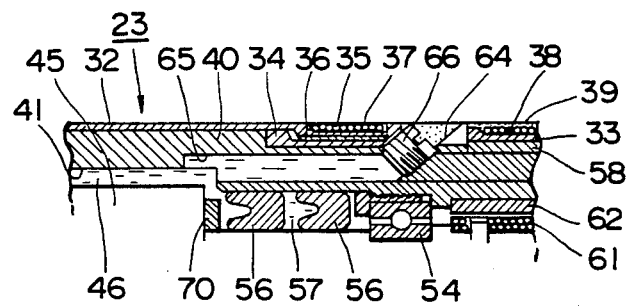

On the other hand, a screw hole 64 is made diagonally forward inward as FIG. 7 and FIG. 8 from a part of the outer peripheral surface of the above mentioned ring-shaped connecting fixing member 34 toward the tip block 40 inside it. A communicating pasage 65 communicating with the housing chamber filled with the transmitting medium 46 around the mirror 45 is formed longitudinally forward from the tip of this screw hole 64. A plug 66 is screwed and contained in the above mentioned screw hole 64 so that, when this plug 66 is removed, a smaller diameter tube will be able to be inserted into the screw hole 64 to easily remove bubbles produced within the transmitting medium 46 and to easily replace the transmitting medium 46.

Figure 9:
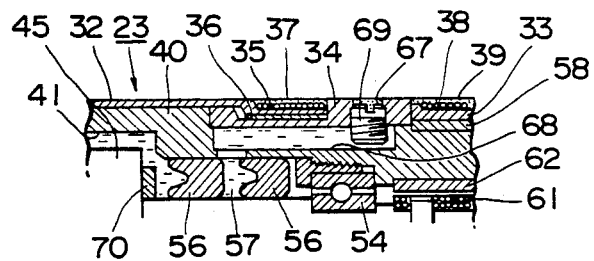

Further, as shown in FIGS. 7 and 9, a screw hole 67 is made as directed toward the inside tip block 40 in a position different from that of the above mentioned screw hole 64 on the outer peripheral surface of the above mentioned connecting fixing member 34, is extended out forward in the lengthwise direction from the tip and is extended at the tip inward to form a communicating passage 68 communicating with the grease charged chamber 57. A plug 69 is screwed and contained in the above mentioned screw hole 67 so that, when this plug 69 is removed, the grease will be able to be easily replaced.

A member 70 annularly fitted to the shaft 44 adjacently to the end of the mirror 45 base is provided to prevent the sealing member 56 from moving forward and can be omitted by extending the base side of the mirror 45 rearward.

The operation of the thus formed embodiment shall be described in the following.

As shown in FIG. 3, the optical sighting tube 27 is inserted into the guide tube of the ultrasonic wave probe body 21 so that the forward and right side forward views can be observed through the incised window 25 by the observing optical system arranged in the tip part of the optical sighting tube 27. The cable 30 extending out of the holding grip 29 is connected to the observation indicating device through separate unit containing the pulse oscillator or the like. The light guide cable is connected to the optical sighting tube 27 so that the illuminating light can be fed from the light source device.

In the above mentioned state, the ultrasonic wave probe body 21 is fitted to a trocar and is introduced into a body cavity to observe an object with the optical sighting tube 27 and the transmitting and receiving window 52 is pushed against object such as an internal organ. In such case, if the bendable portion 24 is curved to the right, the ultrasonic wave probe head 23 and transmitting and receiving window 52 together with such object as the internal organ will be able to be brought into the center of the visual field.

With the window pushed against the internal organ, when the motor within the holding grip 29 is rotated and driven, the rotation will be transmitted to the hard shaft inserted through the ultrasonic wave probe body 21 through the soft shaft not illustrated, the rotation of this hard shaft will be transmitted to the soft shaft 61 near the incised window 25 the rotation of this soft shaft 61 will be further transmitted to the second and first shafts 53 and 44 and the mirror 45 fitted to the tip of the first shaft 44 will be rotated and driven.

When the above mentioned mirror 45 is rotated, as pulses exciting ultrasonic waves are fed in turn to the ultrasonic wave oscillator 42 through the cable 51, the ultrasonic wave beam emitted from the transmitting and receiving surface 42A will be reflected by the mirror 45 through the transmitting medium 46 and will be further emitted to the side of the internal organ in contact with the outer peripheral surface of this transmitting and receiving window 52 from the transmitting and receiving window 52 through the transmitting medium 46. The ultrasonic wave beam emitted to the side of the internal organ will propagate and will be gradually reduced in the intensity by absorption but will be reflected by the discontinuous boundary surface of the acoustic impedance. A part of it will become an ultrasonic wave echo signal, and will be again reflected by the mirror 45 and will be incident upon the ultrasonic wave oscillator 42. The ultrasonic wave echo signal having entered the ultrasonic wave oscillator 42 will be converted to an electric signal by the ultrasonic wave oscillator and will be amplified by the head amplifier (not illustrated) within the holding grip 29 through the cable 51. The signal prevented by this amplification from reducing in the signal/noise ratio will be transmitted to the observation indicating device, will be modulated in the brightness on an indicating device such as a Braun tube together with a sweep signal synchronized with the rotating position of the mirror 45 detected by the rotation detector (not illustrated) within the holding grip 29 or will be converted so that the reflection strength will vary the hue and will be indicated as an ultrasonic wave fault image.

In the embodiment formed to thus operate, as the tip block 40 corresponding to the outer tube 10 in the above described conventional example is covered to be fitted with the jacket cover 32, the space in which bubbles enter the outer peripheral surface of the tip block in which bubbles are hard to remove will be eliminated. The communicating hole 65 passes through the tip block 40 within from a part of the outer periphery of the connecting fixing member 34 formed in the outer peripheral part at the rear end of the ultrasonic wave probe head 23, communicates with the housing chamber 41 charged with the transmitting medium 46 and able to be opened and closed with the plug 66. If this communicating hold 65 is made to be on the upper side, when the plug 66 is unscrewed, bubbles produced within the housing chamber 41 will be able to be easily removed out of the communicating hole. Also, even when the transmitting medium 46 within the housing chamber 41 has decreased, it will be able to be easily supplemented by inserting a smaller diameter tube or the like.

Further, even if the characteristics of the transmitting medium 46 deteriorate due to the variation with the lapse of years, the transmitting medium 46 will be able to be discharged by inserting a smaller diameter tube or the like through the communicating hole 65 and a new transmitting medium 46 will be able to be easily put in.

Further, as the incised recess 47 for collecting bubbles is formed in the mirror 45, if the incised recess 47 is made to be normally in the upper position when the mirror 45 is not being rotated and driven, even if bubbles are produced within the housing chamber 41, the bubbles will be able to be collected in the above mentioned incised recess 47, the bubbles deposited on the mirror surface will be reduced and the collected bubbles will be able to be removed through the above mentioned communicating hole 65.

Further, the embodiment of the above mentioned structure has such many features as are described in the following.

As the mirror 45 fitted to the rotated driven shaft 44 is provided with the guide groove 48 and is removable in the direction at right angles with the axial direction of the shaft 44, when the jacket cover 32 is removed, the mirror 45 will be able to be easily fitted and removed through the opening and the repair and maintenance will be able to be made simply.

Sealing members 56 substantially U-shaped in the cross-section are annularly fitted in the annular air gap between the outer periphery of the above mentioned shaft 44 and the inner peripheral surface of the tip block 40 outside the shaft 44. The grease charged chamber 57 between both sealing members 56 is charged with grease so that the liquid-tightness may be improved to prevent the transmitting medium 46 from leaking to the bearing 54 side and the shaft 44 may be rotated and driven without becoming eccentric. As the communicating path sealed with the closing member by the screw 69 or the like to open and close the opening end facing the outside is formed between the above mentioned grease charged chamber 57 and the outside, even if the grease deteriorates in characteristics due to the use over a long period, the grease will be able to be easily replaced.

As the jacket cover 32 is made small in the outside diameter, it will be easy to insert and remove and the pain given to the patient will be able to be reduced. As the jacket cover 32 is strongly fixed in the opening rear end part with the thread-like member 35 by interposing the soft tube 36 in the recess in the annular connecting fixing member 34 formed on the outer periphery of the probe, in the case of inserting or removing the jacket cover 32, it will be prevented from being separated. Further, in the above mentioned connecting fixing member 34, as the jacket cover 32 on the tip side and the coating tube 33 on the rear side are separately fixed, even in the case the outer periphery of the probe is worn by being inserted and removed or is hurt by disinfection during the use over a long period, only the hurt part will be able to be econimically replaced by unwinding the thread-like member 35 or 38. Further, as the above mentioned outer periphery of the probe is endurable to the disinfectant and the connecting fixing member having a mechanical strength is used, the outer periphery of the probe will be hard to hurt and the life will be able to be made long.

As the rotation detector detecting the rotating position of the mirror 45 is contained within the holding grip 29, the structure of the interior of the ultrasonic wave probe head 23 will be prevented from becoming complicated. Even if the transmitting medium 46 or the grease leaks rearward, the rotation detecting function will not be damaged. As the observation can be made with the fitted optical sighting tube from the incised window 25 in the rear of the bendable portion 24, the ultrasonic wave probe head 23 will be able to be easily set in an objective position while being within the visual field.

As the soft shaft 61 inserted through the bendable portion 24, curvable and transmitting the torque is formed of coils wound reversely to each other in two layers, in whatever direction it is curved, each coil will compensate the other coil to smoothly transmit the torque.

In the above described embodiment, the incised recess 47 is formed in the mirror 45 but can be also provided in the tip block 40 on the wall surface within the housing chamber 41 adjacent to the communicating passage 65.

The communicating passage 65 in the above described embodiment can be opened and closed with the plug 66 screwed into the screw hole 64. However, for example, a cylinder hole may be used instead of this screw hole and the communicating passage 65 may be closed with a piston fitting in this cylinder hole and normally biased inward. In such case, for example, if such resilient member as a spring is interposed on the rear end side of the piston and is screwed with a screw, the communicating passage 65 will be able to be opened and closed. With such formation, even if the volume of the transmitting medium 46 within the housing chamber 41 and the volumes of the housing chamber 41 and the respective members within the housing chamber 41 vary with the temperature of the object or the temperature in disinfection or washing, as the above mentioned piston moves along the communicating passage 65, bad influence of the volume variation such as that the pressure by the transmitting medium 46 becomes abnormally so high or low that the liquid-tightness or airtightness can not be maintained will be able to be prevented.

As described above, the present invention has many features that, as the communicating path communicates with the housing chamber filled with the ultrasonic wave transmitting medium and the outside and can be opened and closed, bubbles produced within the housing chamber can be easily and quickly removed and an ultrasonic wave fault image of a high quality can be always obtained without being adversely influenced by bubbles.

In the described embodiment of present invention, the optical sighting tube is removable but may be made integral to be applied in the same manner.

Also, in the above described embodiment, the mirror 45 is fitted to the rotatable shaft 44 as opposed to the fixed ultrasonic wave oscillator 42 to transmit and receive ultrasonic waves in a sector but the ultrasonic wave oscillator may be fitted directly to the rotary shaft 44 without using the above mentioned mirror 45. In such case, signals can be transmitted to the ultrasonic wave oscillator by contacting a brush with a contact fitted to the rotary shaft.

It is apparent that working modes different in a wide range can be formed without deviating from the spirit and scope of the present invention. The present invention is not restricted by the specific working mode except being limited in the appended claims.

I claim:

1. In a device for diagnosing body cavity interiors with ultrasonic waves said device having a probe, said probe comprising ultrasonic wave oscillator means adapted for transmitting and receiving ultrasonic waves and contained within a housing chamber fixed to a tip end of a tubular member for introduction into a body cavity and coated with a jacket cover, said jacket cover having an ultrasonic wave transmitting window therethrough, an ultrasonic wave transmitting medium filling said housing chamber, a rotated driven shaft in said housing chamber, means on said rotated driven shaft for reflecting waves transmitted by said ultrasonic wave oscillator and for receiving waves reflected thereto for conversion to electric signals, characterized in that said ultrasonic wave reflecting means includes a mirror at the front of said reflecting means and having a reflector surface for receiving and transmitting ultrasonic waves and recess means at the rear of said reflecting means for collecting and holding gas bubbles from said transmitting medium; that said tubular member has a flexible cover, said flexible cover and said jacket cover being fixed, respectively, to ring-shaped fixed members provided in a block between said tubular member and said housing chamber; and, that a communicating path is formed between the interior and the exterior of said housing chamber and is sealed adjacent the exterior of said housing chamber with a closing means within the outside diameter of said jacket cover without projecting there beyond, which closing means can be opened and closed.

2. In a device for diagnosing body cavity interiors with ultrasonic waves according to claim 1 further characterized in that said closing means is formed of a plug to be screwed in a screw hole provided in the communicating path.

3. In a device for diagnosing body cavity interiors with ultrasonic waves according to claim 1 further characterized in that two sealing members substantially U-shaped in cross-section are annularly fitted to said rotated driven shaft and a grease charged chamber charged with grease is formed in said housing chamber between said sealing members.

4. In a device for diagnosing body cavity interiors with ultrasonic waves according to claim 3 further characterized in that said grease charged chamber communicates with the exterior of said housing chamber through a communicating path closed adjacent the exterior of said housing chamber with a closing membber which can be opened and closed, said communicating path and said closing member being with the outside diameter of said jacket cover and not extending therebeyond.

5. In a device for diagnosing body cavity interiors with ultrasonic waves according to claim 1 further characterized in that said jacket cover is fitted in the opening rear end part through a soft tube to a smaller diameter step of a ring-shaped member formed on the outer periphery of the tubular member and is fixed with a thread-like member wound on the outer periphery.

* * * * *